United States Patent
Canty et al.

(10) Patent No.: US 6,771,366 B2
(45) Date of Patent: Aug. 3, 2004

(54) FLUID FLOW CELL

(75) Inventors: Thomas M. Canty, Williamsville, NY (US); Mike F. Rizzo, Blasdell, NY (US); Paul J. O'Brien, East Aurora, NY (US)

(73) Assignee: J.M. Canty Inc., Buffalo, NY (US)

( * ) Notice: Subject to any disclaimer, the term of this patent is extended or adjusted under 35 U.S.C. 154(b) by 0 days.

(21) Appl. No.: 10/264,858

(22) Filed: Oct. 4, 2002

(65) Prior Publication Data

US 2004/0066509 A1 Apr. 8, 2004

(51) Int. Cl.⁷ ................................................. G01N 7/10
(52) U.S. Cl. ...................................................... 356/246
(58) Field of Search ........................... 356/36, 244, 246, 356/440, 436; 250/576, 459.1, 491.1; 422/52, 63, 65, 82.05, 82.68, 102, 104; 359/894, 895, 440

(56) References Cited

U.S. PATENT DOCUMENTS

| | | | |
|---|---|---|---|
| 2,744,487 A | 5/1956 | Moore et al. ............... | 116/117 |
| 3,299,851 A | 1/1967 | Olsen ........................ | 116/117 |
| 3,837,226 A | 9/1974 | Kawawa ...................... | 73/331 |
| 4,245,566 A | 1/1981 | Shimansky et al. ........ | 109/49.5 |
| 4,446,731 A * | 5/1984 | Martin ....................... | 73/334 |
| 4,809,862 A | 3/1989 | Canty ......................... | 220/82 |
| 6,104,483 A | 8/2000 | Sebock et al. .............. | 356/244 |
| 6,359,742 B1 * | 3/2002 | Canty et al. ................ | 359/894 |
| 6,486,947 B2 * | 11/2002 | Modlin et al. .............. | 356/246 |

* cited by examiner

*Primary Examiner*—Tu T. Nguyen
(74) *Attorney, Agent, or Firm*—Davidson, Davidson & Kappel, LLC

(57) ABSTRACT

A flow cell device for observing a fluid including a housing defining an inlet and an outlet and a viewing assembly coupled to the housing. The viewing assembly includes a first viewing member disposed adjacent to an aperture in fluid communication with the inlet and the outlet. The first viewing member is configured to enable a viewing of the fluid in the aperture and is adjustable with respect to the housing so that a thickness of the aperture is variable. In addition, a method for observing a fluid in a flow cell includes passing the fluid through an adjustable aperture that is defined on a first side by a first viewing member that is moveable so that a thickness of the apeture is adjustable. The method also includes viewing the fluid through the first viewing member as the fluid passes through the aperture.

30 Claims, 5 Drawing Sheets

FLUID FLOW CELL

BACKGROUND OF THE INVENTION

The present invention relates generally to fluid inspection systems and particularly to a flow cell device for observing a fluid passing through it. The present invention also relates to a method for observing a fluid in a flow cell.

Various devices have been used for inspecting a fluid inside of process vessels, engine, pipes, hoses, or other fluid-containing receptacles. For example, it is known to use a viewing port on the side of a vessel or pipeline to view its interior. Many such viewing ports employ a glass disk bolted to the side of the vessel or pipe in various configurations. Structurally superior examples of a viewing unit are disclosed, for example, in U.S. Pat. Nos. 4,809,862 and 6,359,742, which are both incorporated by reference herein. Other types of window viewing units are described, for example, in U.S. Pat. Nos. 2,744,487, 3,299,851, 3,837,226 and 4,245,566. For certain industrial processes, it is desired to use instrumentation, such as imaging and measuring systems in conjunction with a viewing device to provide remote analysis of the process conditions. For example, U.S. Pat. No. 4,977,418 describes a camera viewing device that provides remote viewing of a vessel interior.

Many industrial processes involve fluids that contain particles suspended within the fluids. It is desired, for many of these processes, to observe those fluids in order to determined characteristics of the fluids, such as, for example, the size, shape, or color of the particles. Known devices for observing process fluids have not been adequate in providing a safe or accurate solution for observing process fluids. In addition, many of these known devices do not provide precise conditions for presenting the fluid to for optimal viewing.

Known devices have included fixed aperture cells, or cells having an aperture between two opposing plates in which the aperture can only be adjusted offline. Typically, these cells consist of two thin glass plates glued together with a gasket therebetween for forming an aperture. In some cases, a bolted assembly of metal plates may be used to retain the thin glass flow cells. Such a thin glass plate construction, typical of known flow cells, is subject to breakage or leakage. The thickness of the aperture is either unchangeable or can only he changed offline (i.e. it must be first be disconnected from the fluid flow), requiring considerable time and effort. The flow and analysis of the process fluid must cease during that time. The aperture is typically changed by disassembling the flow cell and replacing the gasket with another gasket of a different thickness. Changing the aperture in these cells not only wastes time, but the selection of aperture thickness is limited by the sizes of the available gaskets.

U.S. Pat. No. 6,104,483 (the "'483 patent") describes a fluid inspection system that includes an optical flow cell for use with an imaging system. The optical flow cell described in the '483 patent includes a housing and a pair of two opposing optical plates through which a sample fluid material flows. This optical flow cell again has the disadvantage that the gap between the opposing optical plates is not adjustable and is suitable only for observing fluid samples, as in a laboratory environment, not for on-line use in an ongoing industrial process.

SUMMARY OF THE INVENTION

Precise aperture thickness adjustment is desired for improved viewing and measuring of different characteristics of the same or different process fluids. Changing the aperture thickness using different sized gaskets is time consuming, inexact and often not reliably repeatable. The optimal aperture for observing a fluid will vary depending on which characteristics of the fluid are desired to be observed at any given time. The optimal aperture will also depend on properties of the fluid and of any suspended particles. Characteristics that may be observed include, among others, the turbidity and color of the fluid, as well as the size, shape, density, opaqueness, and color of the particles.

It is also desired to provide a system of observing a fluid with improved ruggedness, durability, and the capability to handle extreme environments, such as high or low pressures and/or high or low temperatures.

The present invention provides a flow cell device for observing a fluid including a housing defining an inlet and an outlet and a viewing assembly coupled to the housing. The viewing assembly includes a first viewing member adjacent to an aperture that is in fluid communication with the inlet and the outlet. The first viewing member is configured to enable a viewing of the fluid in the aperture and is adjustable with respect to the housing so that a thickness of the aperture is variable.

The viewing assembly may also include a second viewing member disposed opposite the first viewing member and the aperture defined between the first and second viewing members. The housing may include a first housing half and a first sealing element may be disposed between the first housing half and the viewing assembly. The viewing assembly may include a first adapter member disposed between the first viewing member and the housing. The viewing assembly may include a second adapter disposed between the second viewing member and the housing.

At least one of the first and second viewing members may be configured to enable an illumination of the fluid in the aperture. Thus, in one case, both viewing and illumination can be performed through the first viewing member. In another case, viewing and illumination can be performed from opposite sides of the aperture.

At least one of the first and second viewing members may include a viewing port and the other of first and second viewing members may include an illumination port. The viewing port and/or illumination port may include a transparent viewing window disposed therein. The transparent viewing window is preferably glass and is fused to a metal portion of one of the first and second viewing members.

The flow cell device may also include a light source coupled to one of the first and second viewing members, which may include a fiber optic bundle, which may be configured to form a ring arrangement, a point arrangement, or a broadly dispersed arrangement at a position adjacent to one of the first and second viewing members. A camera may be coupled to the viewing port of the flow cell device. The camera may also include a light source to provide illumination to the fluid, for those situations in which direct lighting of the fluid from the same direction as the camera provides optimal imaging. In addition, a flow path of the fluid preferably includes a rectangular cross-section when the fluid is in the aperture.

An inlet reservoir in fluid communication with the inlet, may also be included in the flow cell. The inlet reservoir preferably has a greater volume than a volume of the fluid in the aperture. The inlet may be narrower than the thickness of the aperture. The viewing assembly is preferably suitable for containing the fluid at a high pressure, for example a pressure up to 6000 p.s.i. A second inlet and or a second outlet in fluid communication with the aperture may be defined in the housing.

The present invention also provides a method for observing a fluid in a flow cell. The method includes passing the fluid through an adjustable aperture defined, on one side, by a first viewing member that is moveable so that a thickness of the aperture is adjustable. The method also includes viewing the fluid through the first viewing member as the fluid passes through the aperture.

A second side of the aperture may be defined by a second viewing member so that the fluid passes through the two viewing members. The method may also include the step of moving the first viewing member so as to adjust the thickness of the aperture.

The viewing may be performed using a camera coupled to the first or second viewing member. The method may also include illuminating the fluid through either one of the first and second viewing members. The illuminating may be performed using a fiber optic bundle, which may be arranged in a ring-shape, coupled to the first or second viewing member.

BRIEF DESCRIPTION OF THE DRAWINGS

The present invention will be discussed in the following with reference to the drawings, in which following figures show a preferred embodiment of the present invention in which.

DETAILED DESCRIPTION OF A PREFERRED EMBODIMENT

Figure 1:
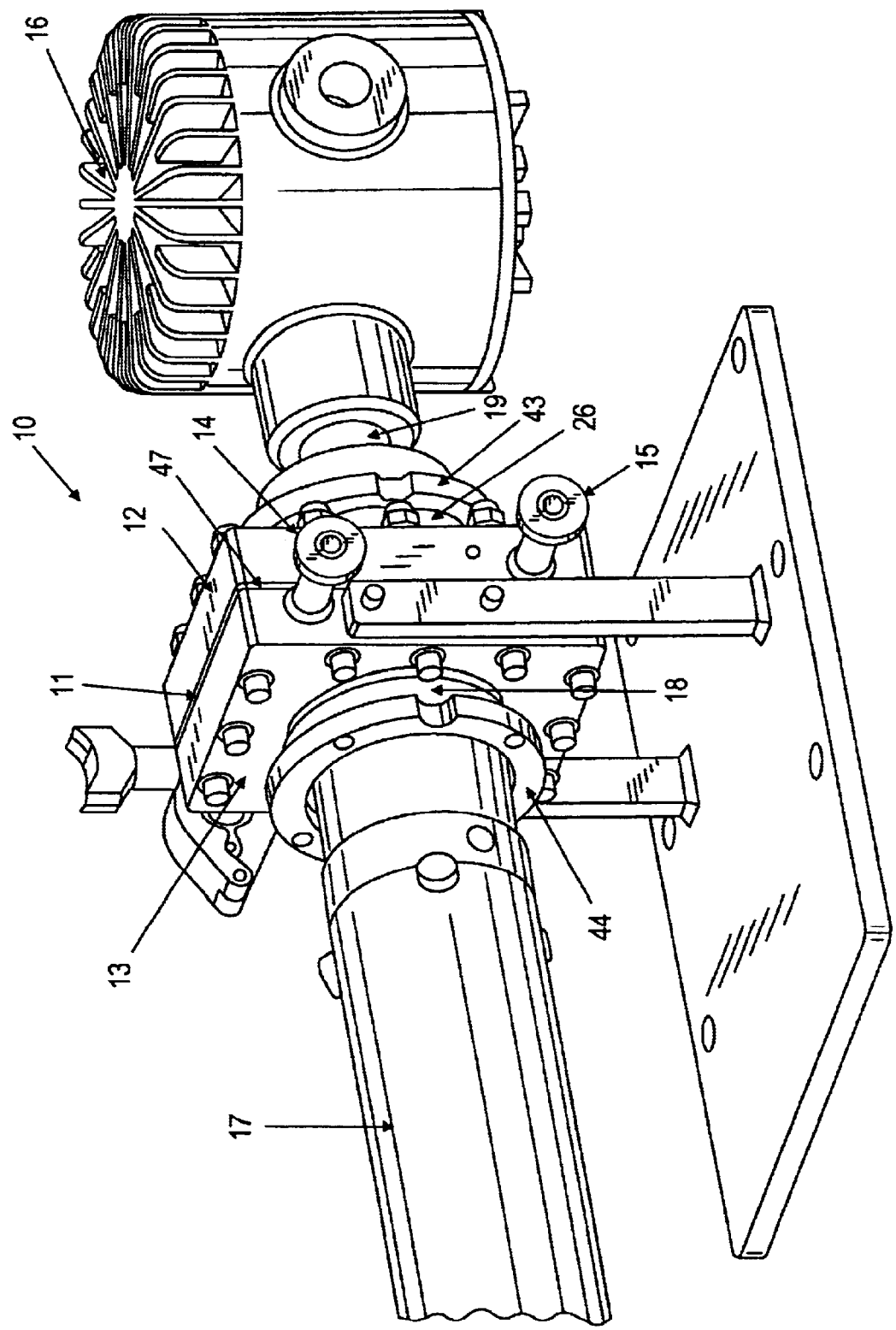
FIG. 1 shows a partial perspective view of a flow cell device according to the present invention.

FIG. 1 shows a partial perspective view of one embodiment of flow cell device 10 according to the present invention. Flow cell device 10 includes housing 11, which consists of first housing half 12 joined together with second housing half 13. A gasket 47 may be disposed between the two housing halves so as to form housing gap 31 between the first and second housing halves. (See FIG. 2). Alternatively, the housing halves may include internal recesses for forming housing gap 31. Second housing half 13 includes inlet conduit 14 which is in fluid communication with housing gap 31 between the two housing halves. First housing half 12 includes outlet conduit 14 which is likewise in fluid communication with housing gap 31 between the two housing halves. Viewing assembly 18 is coupled to housing 11 and includes, in the preferred embodiment first viewing member 26 and second viewing member 28, which are disposed opposite one another so as to form adjustable aperture 23 therebetween, as can be more clearly seen in FIG. 2. It is also recognized that the viewing assembly could include a single viewing member adjustable with respect to the housing and forming an adjustable aperture between the viewing member in the housing. In the preferred embodiment, aperture 23 is formed between viewing members 26 and 28 and is in fluid communication with housing gap 31. However, unlike housing gap 31, aperture 23 is adjustable while the fluid is flowing through the flow cell device, by a moving first viewing member 26 with respect to the housing 11.

Inlet conduit 14 can be attached, for example using a hose or high pressure pipeline, to an inlet source (not shown). The inlet source may be a laboratory vessel containing a sample fluid, or may be an a pipe, engine, or other fluid containing vessel that is integral with an ongoing industrial process. Likewise, outlet conduit 15 can be attached, for example using a hose or high pressure pipeline to an outlet receptacle (not shown). Again, the outlet receptacle may be a laboratory vessel for holding a sample fluid, but may also be a pipe, engine, or other fluid-containing vessel that is integral with an ongoing industrial process. Thus, the flow cell device described in the drawings may be used to observe fluid samples in a laboratory setting, or may be installed on-line to observe fluids directly as they occur during an ongoing industrial process. A pump, or other pressure creating device may be used in conjunction with the flow cell device 10, in order to cause the fluid to flow through the device. Alternatively, either gravity or the fluid pressures inherent in the online process will cause the desired flow.

Light source 16 may be coupled to first viewing member 26 in order to illuminate the fluid as it flows in the aperture 23. Viewing and illumination can also take place through the same port. Light source 16 includes light pipe 19, which, in this embodiment, contains fiber optic bundles that carry the light to first viewing member 26. In this embodiment, the light source includes an incandescent bulb emitting visible white light. However, a variety of light sources may be used emitting light from across the visible and non-visible spectrum to illuminate the fluid in the aperture. The light source may include any of a number of sources for emitting the light including, for example, various types of light bulbs, lasers, light emitting diodes, reflection of ambient light, and light emitting chemical reactions.

Figure 2:
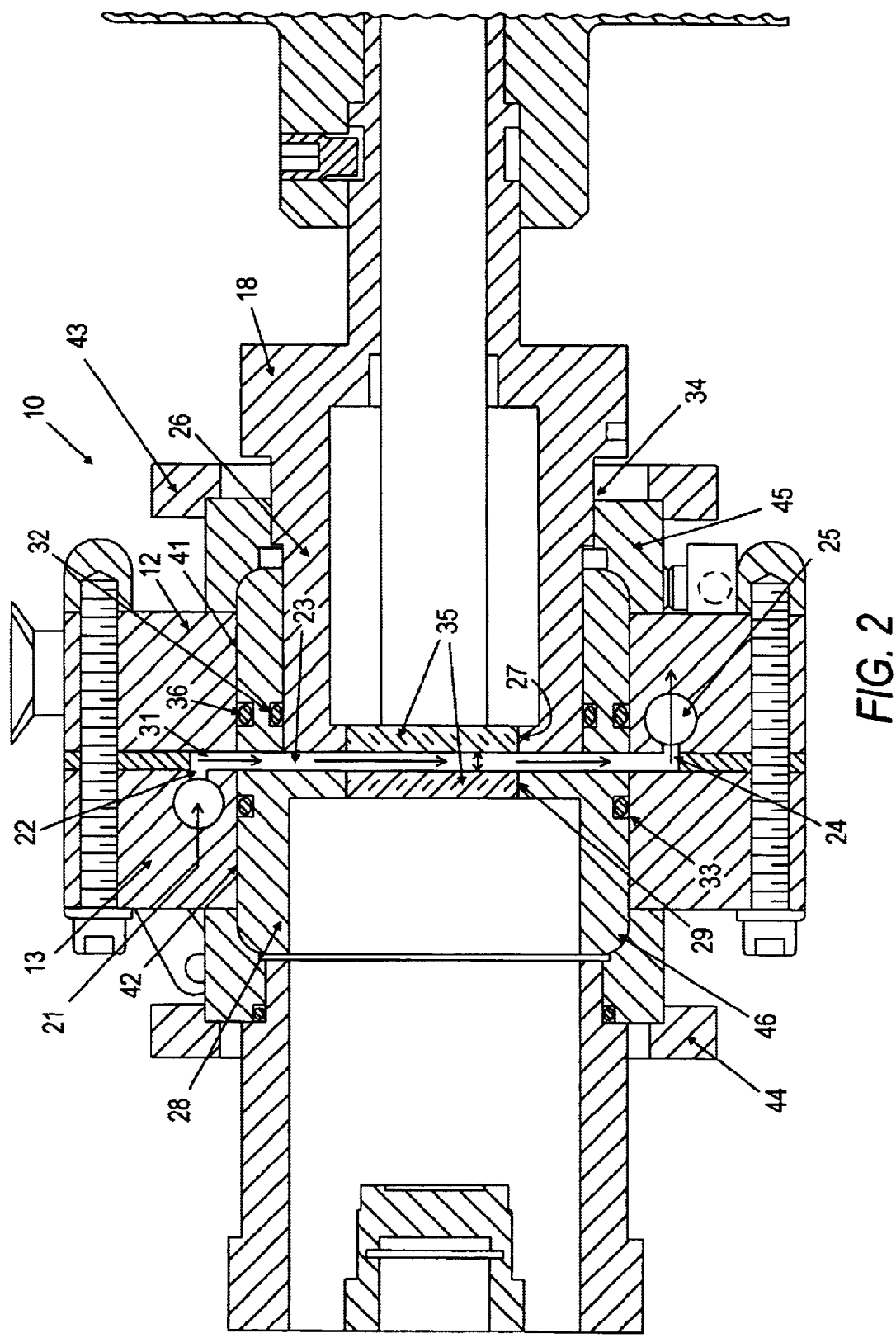
FIG. 2 shows a partial section view of the flow cell device of FIG. 1.

As shown in FIG. 2, after passing through the inlet conduit 14 (shown in FIG. 1), the fluid enters inlet reservoir 21 which is formed in an interior portion of second housing half 13. From the inlet reservoir, the fluid passes through inlet 22 into housing gap 31 between first and second housing halves 12, 13. From housing gap 31, the fluid passes through aperture 23 defined, in this embodiment, as the space between first viewing member 26 and second viewing member 28. In the embodiment shown in the figures, viewing assembly 18 includes first and second viewing members 26, 28. The viewing assembly 18 is coupled to first housing half 12 at first viewing assembly opening 41 in housing half 12. The viewing assembly 18 includes first adapter element 45 which is coupled to the first housing half 12 with the help of first flange 43, which may be bolted to first housing half 12. First scaling element 36 is disposed between first adapter member 45 of viewing assembly 18 and housing half 12 so that fluid may not escape through opening 41. Second sealing element 32 is disposed between first viewing-member 26 and first adapter member 45. The viewing assembly 18 is also coupled to second housing half 13 at second viewing assembly opening 42 in housing half 13. The viewing assembly 18 includes a second adapter member 46, which is secured to housing half 13 with the help of second flange 44, which may be bolted to second housing half 13. Third sealing element 33 is disposed between second adapter member 46 of viewing assembly 18 and housing half 13 so that fluid may not escape through opening 42.

As shown in FIG. 1, light source 16 is coupled to first viewing member 27 to illuminate the fluid in aperture 23 and camera 17 is coupled to second viewing member 28. Thus, in the preferred embodiment, the viewing is performed using the camera 17. Camera 17 may be any kind of camera, such as, for example, a still camera, a video camera, or a CCD camera, and may transmit the image to a remote location, where it can be observed, for example on a video monitor. The image may also be sent as an electronic file to a microprocessor, where various measurements, analysis and calculations are made to the image information. A person of ordinary skill in the art would recognize that viewing could be performed with or without instrumentation such as a camera from either or both viewing elements. Similarly, illumination of the fluid could be performed, through either or both of the viewing elements, or with no special lighting apparatus, such as allowing ambient light to shine through one or both of the viewing members. Though both members 26 and 28 are referred to as viewing members, it is not necessary that both members enable a viewing of the fluid. In the preferred embodiment, as discussed below, viewing member 28 enables a viewing of the fluid through camera 17, and viewing member 26 enables an illumination of the fluid using light source 16. It is also not necessary that the two viewing members enable either viewing or illumination. For example, one viewing member may be made of solid steel and enable neither, such that viewing and/or viewing and illumination are carried out through the other viewing member.

In the preferred embodiment, first and second viewing members 26, 28 each define viewing ports 27 and 29 respectively. Disposed within each viewing port is a transparent glass window 35 to allow illumination and or viewing of the fluid in aperture 23. The surface of each window toward the aperture is preferably flush with a surface of the respective viewing member 26, 28. The glass windows 35 are preferably fused directly to an annular metal frame, for example as described in U.S. Pat. No. 6,359,742. Thus, the glass windows 35 can be directly to a metal end portion of the respective viewing member 26, 28, shaped to form an annular frame. Preferably the construction is sturdy enough to handle fluids having high pressures, such as pressures of up to 6000 p.s.i. The sturdy fused glass to metal construction enables a wide field of view for a broader view of the flow stream and thus better analytical accuracy, and a larger flow cell to process more fluid in less time. The sturdy construction also enables the device to be employed in rugged field environments, such as when vibration and other ambient effects are present that might cause a thin glass window flow cell to leak or break.

In the preferred embodiment, the first viewing member 26 is adjustable with respect to the second viewing member 28 so as to vary a thickness t, of aperture 23. First adapter member 45 and first viewing member each include a corresponding threaded area 34. Thus, by rotating the first viewing member 26 within adapter member 45 (which is fixedly mounted to the housing), the position of first viewing member 26 is changed with respect to the housing and second viewing member 28, thus changing thickness t of aperture 23. In the preferred embodiment, the adjustment can be performed while the fluid is flowing through the device 10, and while viewing the fluid in aperture 23. In addition, the threading allows very precise positioning of the viewing member 26, and thus very exact sizing of thickness t of aperture. In the preferred embodiment, the second viewing member is fixedly attached to the second adapter member 46, which is fixedly attached to second housing half 13. Without departing from the present invention, the flow cell could alternatively be constructed so that the second viewing member was adjustable instead, or so that both the first and second viewing members were adjustable, or with a single viewing member forming an adjustable aperture between the single viewing member and a wall of the housing. In addition, there are a number of mechanisms for enabling one or both viewing members to be adjusted with respect to one another. The adjustment mechanism for the viewing members may also be automatic. For example, the position of the viewing members could be cycled to form first a narrow then wide aperture so as to capture particles of interest between the viewing members for viewing, then releasing them and capturing a new volume of sample. The adjustment mechanism may also be controllable from a remote location, such as from a monitoring control room.

It is often desired to adjust the aperture thickness t several times to find the optimal viewing conditions and so that specific characteristics of the fluid are discernible. This may also be desirable, for example, if the characteristics of the fluid vary with flow, or it is desired to observe particles having various characteristics within the same fluid. The surfaces of the viewing members and glas windows are preferably flat and parallel at the aperture 23. This provides a flow stream that is of constant thickness and the fluid remains a constant distance from a viewing apparatus such as camera 17. This can be important for gathering accurate and consistent measurements. For example, when measuring particle size, two particles of the same size at significantly different distances from the viewing means may appear to have different sizes.

Figure 3:
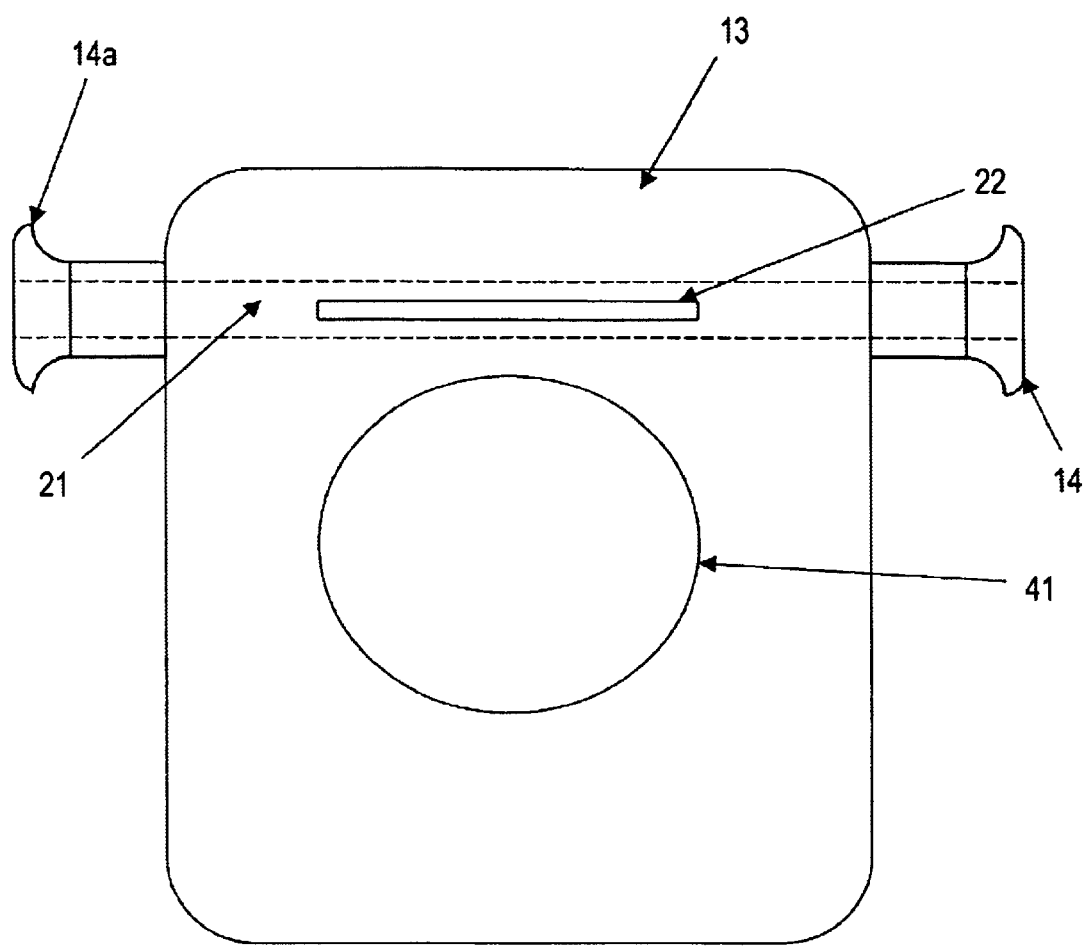
FIG. 3 shows a second housing half of the flow cell device of FIG. 1.

FIG. 3 shows a front view of second housing half 13 without the rest of the flow cell device 10. As shown, inlet 14 conduit connects to inlet reservoir 21, which is a space in the interior portion of housing half 13. In this embodiment a second inlet 14a also joins inlet reservoir 21. Two (or more) inlet conduits can be used in order to allow fluids from two different sources to be analyzed, with the two fluids mixing in reservoir 21 just before passing through inlet 22 into housing gap 31. This may be useful, for example for time-sensitive or atmospheric-sensitive characteristics of fluid mixtures, which would be difficult to view if they had to be mixed in advance. Preferably, the volume of inlet reservoir 21 is greater than the volume between housing halves 12 and 13 (i.e. the volume of the fluid in housing gap 31 and aperture 23). In addition, a long thin inlet opening 22 is preferable to provide an even flow field across the width of the flow cell. Second housing half 13 defines second viewing assembly opening 41, inside which the viewing assembly 18 may be disposed.

Figure 4:
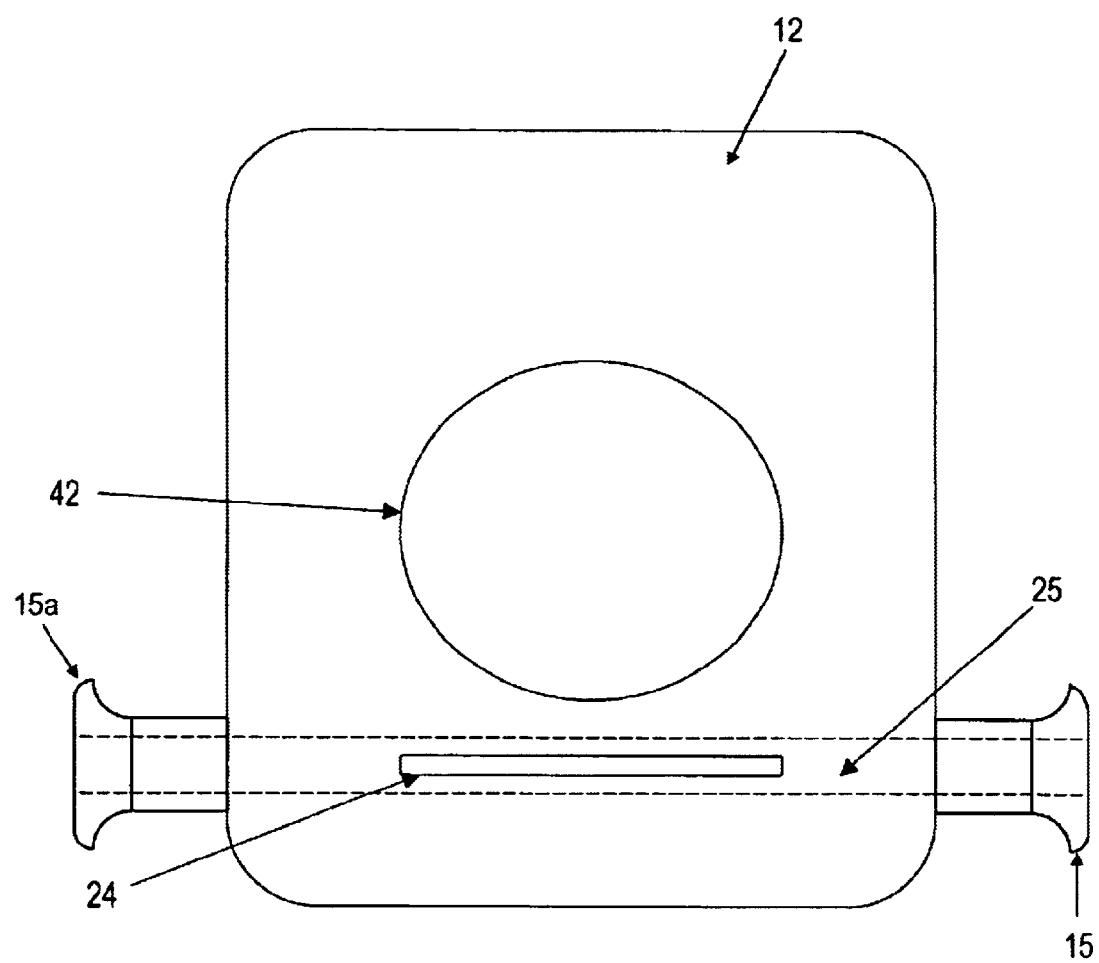
FIG. 4 shows a first housing half of the flow cell device of FIG. 1.

FIG. 4 shows a front view of first housing half 12, which includes first viewing assembly opening 42 inside of which the viewing assembly 18 may be disposed. Opening 42 is positioned in a central region of first housing half 12 so that it aligns across from second viewing member opening 41, when the two housing halves are joined together. After flowing through aperture 23, the fluid flows out of outlet 24 into outlet reservoir 25. The fluid may then flow out both of outlet conduit 15 and second outlet conduit 15a.

Figure 5A:
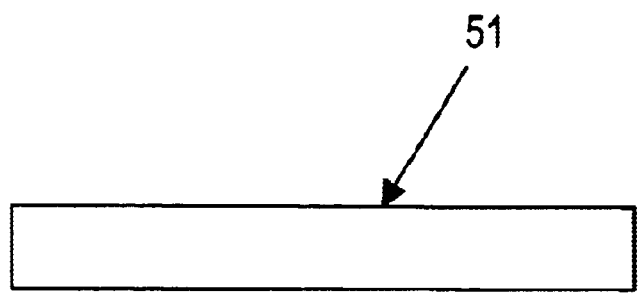
FIGS. 5a and 5b show schematic views of a standard fiber optic bundle.
Figure 5B:
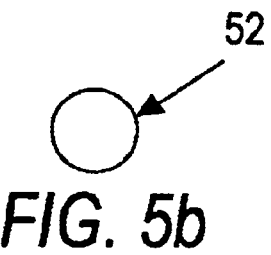

FIGS. 5a and 5b show side and end views of fiber optic bundle 51. Reference numeral 51 refers to a standard fiber optic bundle in which the fibers are generally evenly distributed in a cylindrical form. Thus, the end 52 of the standard fiber optic bundle is forms a circle of light. The end of the fiber optic bundle is preferably placed adjacent one of the viewing members in order to illuminate the fluid in the aperture.

Figure 6A:
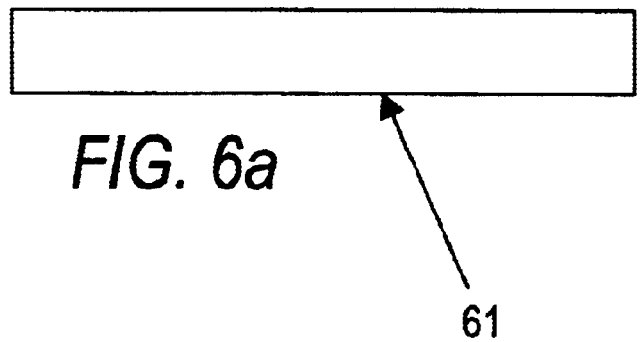
FIGS. 6a and 6b show a schematic views of a fiber optic bundle having a ring arrangement.
Figure 6B:
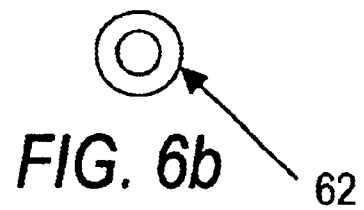

FIGS. 6a and 6b show a ring fiber optic bundle in which the fibers are arranged in a ring shape in an outer area of a cylinder. Thus the end 62 of ring fiber optic bundle 61 forms a ring of light. The inventors have discovered that this formation provides light into the flow cell at an angle, which allows particles in the fluid to be illuminated by partial side light. In many cases, partial side lighting creates better visibility of the particles.

In the preceding specification, the invention has been described with reference to a specific exemplary embodiment thereof. It will, however, be evident that various modifications and changes may be made thereto without departing from the broader spirit and scope of the invention as set forth in the claims that follow. The specification and drawings are accordingly to be regarded in an illustrative rather than a restrictive sense.

What is claimed is:

1. A flow cell device for observing a fluid, the device comprising:

a housing defining an inlet and an outlet; and a viewing assembly coupled to the housing, the viewing assembly including a first viewing member disposed adjacent to an aperture, the aperture in fluid communication with the inlet and the outlet;

wherein the first viewing member is configured to enable a viewing of the fluid in the aperture, and is adjustable with respect to the housing so that a thickness of the aperture is variable.

2. The flow cell device as recited in claim 1 wherein the viewing assembly includes a second viewing member disposed opposite the first viewing member and the aperture is defined between the first and second viewing members.

3. The flow cell device as recited in claim 2 wherein the viewing assembly includes a second adapter member disposed between the second viewing member and the housing.

4. The flow cell device as recited in claim 2 wherein at least one of the first and second viewing members is configured to enable an illumination of the fluid in the aperture.

5. The flow cell device as recited in claim 2 wherein the first viewing member is configured to enable the viewing of the fluid in the aperture and the second viewing member configured to enable an illumination of the fluid in the aperture.

6. The flow cell device as recited in claim 2 wherein at least one of the first and second viewing members includes a viewing port.

7. The flow cell device as recited in claim 6 wherein the other of first and second viewing members includes an illumination port.

8. The flow cell device as recited in claim 6 wherein the viewing port includes a transparent viewing window disposed therein.

9. The flow cell device as recited in claim 8 wherein the transparent viewing window is fused to a metal portion of one of the first and second viewing members.

10. The flow cell device as recited in claim 7 wherein the illumination port includes a transparent illumination window disposed therein.

11. The flow cell device as recited in claim 10 wherein the transparent illumination window is fused to a metal portion of one of the first and second viewing members.

12. The flow cell device as recited in claim 6 further comprising a camera coupled to the viewing port.

13. The flow cell device as recited in claim 2 further comprising a light source coupled to one of the first and second viewing members.

14. The flow cell device as recited in claim 13 wherein the light source includes a fiber optic bundle.

15. The flow cell device as recited in claim 14 wherein the fiber optic bundle forms a ring arrangement at a position adjacent to one of the first and second viewing members.

16. The flow cell device as recited in claim 1 wherein the housing includes a first housing half and the flow cell device further comprises a first sealing element disposed between the first housing half and the viewing assembly.

17. The flow cell device as recited in claim 1 wherein the viewing assembly includes a first adapter member disposed between the first viewing member and the housing.

18. The flow cell device as recited in claim 1 wherein a flow path of the fluid includes a rectangular cross-section when the fluid is in the aperture.

19. The flow cell device as recited in claim 1 further comprising an inlet reservoir in fluid communication with the inlet, the inlet reservoir having a greater volume than a volume of the aperture.

20. The flow cell device as recited in claim 19 wherein the housing defines first and second inlet conduits in fluid communication with the inlet reservoir.

21. The flow cell device as recited in claim 1 wherein the inlet is narrower than the thickness of the aperture.

22. The flow cell device as recited in claim 1 wherein the viewing assembly is suitable for containing the fluid at a pressure up to 6000 p.s.i.

23. The flow cell device as recited in claim 1 wherein the housing defines first and second outlet conduits and an outlet reservoir in fluid communication with the outlet conduits and the inlet.

24. A method for observing a fluid in a flow cell, the method comprising:

passing the fluid through an adjustable aperture, a first side of the adjustable aperture being defined by a first viewing member, the first viewing member being moveable so that a thickness of the aperture is adjustable; and viewing the fluid through the first viewing member as the fluid passes through the aperture.

25. The method as recited in claim 24 wherein a second side of the adjustable aperture is defined by a second viewing member.

26. The method as recited in claim 25 wherein the viewing is performed using a camera coupled to one of the first and second viewing members.

27. The method as recited in claim 25 further comprising illuminating the fluid through one of the first and second viewing members.

28. The method as recited in claim 27 wherein the illuminating is performed using a fiber optic bundle coupled to one of the first and second viewing members.

29. The method as recited in claim 28 wherein the fiber optic bundle is disposed in a ring arrangement adjacent one of the first and second viewing members.

30. The method as recited in claim 24 further comprising moving the first viewing member so as to adjust the thickness of the aperture.

* * * * *